United States Patent
Boehm, Jr. et al.

(10) Patent No.: US 10,517,603 B2
(45) Date of Patent: Dec. 31, 2019

(54) ENDOVASCULAR CATHETER WITH MULTIPLE CAPABILITIES

(71) Applicant: Cosette, Lee & Harrison, LLC, New Hartford, NY (US)

(72) Inventors: Frank H. Boehm, Jr., New Hartford, NY (US); Janice L. Stone, New Hartford, NY (US)

(73) Assignee: COSETTE, LEE & HARRISON, LLC, New Hartford, NY (US)

( * ) Notice: Subject to any disclaimer, the term of this patent is extended or adjusted under 35 U.S.C. 154(b) by 506 days.

(21) Appl. No.: 15/195,180

(22) Filed: Jun. 28, 2016

(65) Prior Publication Data
US 2017/0000493 A1    Jan. 5, 2017

Related U.S. Application Data

(60) Provisional application No. 62/186,441, filed on Jun. 30, 2015.

(51) Int. Cl.
*A61B 17/12*    (2006.01)
*A61F 2/01*    (2006.01)
(Continued)

(52) U.S. Cl.
CPC .. *A61B 17/12113* (2013.01); *A61B 17/12136* (2013.01); *A61B 5/026* (2013.01);
(Continued)

(58) Field of Classification Search
CPC .......... A61F 2002/011; A61F 2002/016; A61F 2002/018; A61B 17/12045;
(Continued)

(56) References Cited

U.S. PATENT DOCUMENTS

| | | |
|---|---|---|
| 4,581,017 A | 4/1986 | Sahota |
| 4,763,654 A | 8/1988 | Jang |

(Continued)

FOREIGN PATENT DOCUMENTS

WO    WO199846309    10/1998

OTHER PUBLICATIONS

ISA/US; International Search Report/Written Opinion (ISR/WO) from corresponding PCT application No. PCT/US16/39780 as completed Sep. 15, 2016 (total 9 pages).

(Continued)

*Primary Examiner* — Sarah A Simpson
(74) *Attorney, Agent, or Firm* — Christopher E. Banks; Schmeiser, Olsen & Watts, LLP

(57) ABSTRACT

An endovascular catheter combination configured to have multiple capabilities is disclosed. These capabilities include proximal and distal occlusion of a segment of a target blood vessel (such as the carotid artery) thus excluding the segment of the blood vessel from circulation for purposes such as surgical consideration. Another capability includes intravascular shunting of the blood through the excluded portion of the artery during a procedure such as an endarterectomy. Additionally, a microsensor provides a measurement of the rate/volume of blood flow through the distal end of the catheter. In one embodiment, a guidewire is provided with a filtration mesh as an anti-embolic mechanism both at the time of initial positioning of the catheter and after reversing the occlusion.

2 Claims, 20 Drawing Sheets

(51) Int. Cl.
*A61B 5/026* (2006.01)
*A61B 17/22* (2006.01)

(52) U.S. Cl.
CPC ............... *A61B 2017/1205* (2013.01); *A61B 2017/22045* (2013.01); *A61F 2/013* (2013.01)

(58) Field of Classification Search
CPC ....... A61B 17/12113; A61B 17/12136; A61M 2025/1095
See application file for complete search history.

(56) References Cited

U.S. PATENT DOCUMENTS

| | | |
|---|---|---|
| 4,771,777 A | 9/1988 | Horzewski et al. |
| 4,850,358 A | 7/1989 | Millar |
| 5,019,042 A | 5/1991 | Sahota |
| 5,281,200 A | 1/1994 | Corso, Jr. et al. |
| 5,370,617 A | 12/1994 | Sahota |
| 5,395,333 A | 3/1995 | Brill |
| 5,536,250 A | 7/1996 | Klein et al. |
| 5,599,307 A | 2/1997 | Bacher et al. |
| 5,876,367 A * | 3/1999 | Kaganov ................ A61B 17/22 604/8 |
| 6,656,154 B1 | 12/2003 | Addis |
| 8,152,782 B2 | 4/2012 | Jang et al. |
| 8,444,665 B2 | 5/2013 | Tsugita |
| 2001/0001825 A1 | 5/2001 | Snow et al. |
| 2002/0042625 A1 | 4/2002 | Stack et al. |
| 2002/0091409 A1 | 7/2002 | Sutton et al. |
| 2002/0128679 A1* | 9/2002 | Turovskiy ............... A61F 2/013 606/200 |
| 2002/0169413 A1 | 11/2002 | Keren et al. |
| 2003/0120304 A1 | 6/2003 | Kaganov et al. |
| 2005/0015048 A1* | 1/2005 | Chiu ..................... A61M 25/10 604/101.04 |
| 2006/0224176 A1 | 10/2006 | Fung et al. |
| 2007/0078505 A1 | 4/2007 | Dimitrov |
| 2011/0190727 A1 | 8/2011 | Edmunds et al. |
| 2013/0184742 A1* | 7/2013 | Ganesan ................. A61F 2/01 606/200 |
| 2014/0012306 A1 | 1/2014 | Zhadkevich |

OTHER PUBLICATIONS

EPO; Extended European Search Report for corresponding European Application 16818584.1; dated Mar. 27, 2019.

* cited by examiner

ENDOVASCULAR CATHETER WITH MULTIPLE CAPABILITIES

CROSS-REFERENCE TO RELATED APPLICATIONS

This application claims priority to and is a non-provisional of U.S. Patent Application Ser. No. 62/186,441 (filed Jun. 30, 2015) the entirety of which is incorporated herein by reference.

BACKGROUND OF THE INVENTION

The subject matter disclosed herein relates to the general field of endovascular catheters used to treat vascular pathologies and specifically to an endovascular catheter with multiple capabilities which can serve as an adjunct to surgery on vascular structures.

Stroke has plagued mankind since time immemorial. Its sudden and devastating effects were first recognized stroke as a pathologic entity by Hippocrates, often referred to as the Father of Medicine, over 2,400 years ago. Plato, Pope St. Leo, Charlemagne, Henry VIII, Woodrow Wilson, Vladimir Lenin, Sir Walter Scott, Richard Nixon and Margaret Thatcher are but a handful of historic figures who met their end as the result of stroke. Diligent postmortem studies demonstrated areas of the brain which had infarcted, presumably from interruption in circulation, although it took another seven decades to ultimately recognize that disease of the carotid arteries—which supply the majority of blood flow to the brain—was responsible for this malady in the majority of cases. Specifically, it is now known that atherosclerotic plaque along the walls of the internal carotid artery, usually just beyond the bifurcation of the common carotid artery, leads to narrowing of the lumen of the artery. This can result in stroke in two ways: first, the plaque can narrow the lumen to a dangerous point, and second, pieces of the plaque can break off, forming globules referred to as emboli.

In the first scenario, the lumen can be narrowed to a critical point, reducing the blood flow to a point that it now longer meets the metabolic demands of the brain, causing a temporary reduction in brain function. A reflex increase in the muscle tone in the arteries can restore the blood flow after a few minutes, sometimes preventing further damage. Clinically, this sequence of events can initially result in a transient but fully reversible loss of neurologic function, a phenomenon known as a "Transient Ischemic Attack," and more commonly known as a "TIA," or "Mini-Stroke." It is known that this phenomenon often heralds or is a precursor to a major stroke. If such a critical reduction of blood flow continues, an extensive blood clot can form within the carotid artery, resulting in extensive permanent loss of blood flow and massive damage to the brain, clinically resulting in a stroke.

In the second scenario, the emboli break off and are then carried upstream where the arteries become smaller and smaller until a point is reached where the arteries become so small that these emboli cannot pass through. If the emboli are tiny, this may be insignificant. On the other hand, if the emboli are massive, they become lodged at a point where they stop blood flow to a major portion of the cerebral circulation, resulting in the loss of blood flow to large areas of the brain. It became apparent that if treatment could be instituted at a point when the patient first becomes symptomatic with TIA's perhaps the permanent damage from a stroke could be avoided.

On that basis, in 1953 the great cardiovascular surgeon Michael De Bakey performed the first carotid endarterectomy (CEA). This is a surgical procedure in which the surgeon temporarily clamps off the common, internal and external carotid arteries and then incises the affected artery and removes the offending plaque prior to sewing the artery closed. By the 1980's, this had become one of the cornerstones in the treatment of stroke. However, a "double-edged sword" is that although CEA is performed to prevent future strokes in a patient, stroke is also the main complication CEA. Specifically, the rate of stroke as a complication of this surgery ranges from 2-7%. This is thought to be related to either the temporary loss of blood flow to the cerebral hemisphere, or emboli arising from manipulation of the artery.

In an attempt to reduce the perioperative stroke rate, the 1970's witnessed the introduction of intraoperatively placing a tube or "intravascular shunt," which carries blood from the common carotid artery at a point prior to where the artery is clamped off to the internal carotid artery at a point beyond where this artery is clamped off, and thus maintain flow to the brain. However, the use of intraoperative/intravascular shunting remains controversial. While the theoretical basis for the use of shunting is recognized by all, detractors of this technique point out that large, controlled studies have never proven, incontrovertibly, that shunting reduces the perioperative stroke rate. Moreover, a number of technical difficulties associated with the use of shunts have been cited by multiple authors. These shortcomings include the technical difficulties in positioning the shunt, the variability of time required for the placement, the inconstancy of the blood flow during surgery, and the need to clamp off the carotid to introduce and remove the shunt. With a persisting stroke rate being reported even with the use of intravascular shunts, the question of whether CEA was truly better than medical therapy alone needed to be addressed.

The discussion above is merely provided for general background information and is not intended to be used as an aid in determining the scope of the claimed subject matter.

BRIEF DESCRIPTION OF THE INVENTION

The present invention is therefore provided to address the needs and goals disclosed above, as well as others. To that end, the invention discloses an endovascular catheter system which achieves these multiple objects in a unique, useful, novel and nonobvious fashion.

One aspect of the invention is an endovascular catheter which is designed to be inserted through any artery or vein, such as the brachial or radial arteries and especially the femoral artery, using a Seldinger technique to study the carotid and is radiographically guided into the target carotid artery in such a way that the leading end has been guided past the target surgical area of plaque/stenosis.

In particular, it is anticipated that placement of the catheter would be achieved by initial placement of a guidewire, said guidewire having important characteristics which would include a limited diameter such that it could be negotiated past the most severe areas of stenosis without creating an injury to the plaque; other important characteristics would include a soft, flexible nature which would again limit the possibility of creating an injury to the plaque stenosis. Furthermore, there would be, in the ideal embodiment, a deployable/expandable filtration net which would be deployed once the guidewire was in final position. Said net would be deployed prior to passage of the catheter, anticipating the (albeit small) possibility that positioning the catheter could result in injury to the plaque with consequent embolus formation and distal embolization; the net would be positioned to capture and ultimately retrieve any such embolus. This net would also, of course, capture any emboli created by the surgical manipulation. It has been postulated that there may be debris which serves as a source of emboli after removal of the plaque/stenosis. Therefore, as taught by Tsugita in U.S. Pat. No. 8,444,665, as well as Jang et al in U.S. Pat. No. 8,152,782 and others, the use of such a mesh may be beneficial in preventing the morbidity and mortality associated with postoperative embolic phenomena. In another embodiment, the catheter is designed so that it is disposed over a guidewire, said guidewire being provided with the mesh-like anti-embolic feature as well as being configured in deploy this mesh.

This catheter is provided with a series of balloon occludes, as taught be Addis in U.S. Pat. No. 6,656,154 and others. The invention is provided with a first elastomeric occluder such as an inflatable/deflatable balloon which surrounds the outer surface of the catheter at its leading end which shall be known as the internal carotid balloon. When the catheter is in its final position and poised to be deployed, this balloon would be positioned within the internal carotid artery at a point beyond, or "upstream" from the target surgical area. Also provided is a second balloon, the common carotid balloon, which, in the desired position, would be located within the common carotid artery and hence prior to or "downstream" from the target surgical area. When both of these are inflated to the optimum pressure/volume, and in concert with external occlusion of the external carotid artery, the blood flow through the target area would be excluded hence providing the surgeon with a "bloodless," operative field in order to remove the plaque/stenosis. Alternative embodiments of the arrangement of said balloons can be envisioned, with all such embodiments being included within the spirit and scope of the invention.

In a different aspect of the invention, the catheter between these two balloons is provided with a lumen which is continuous with the lumen of the catheter prior to the common carotid balloon. In U.S. Pat. No. 4,581,017, Sahota teaches that a catheter with side apertures proximally and distally to an angioplasty balloon so that blood flow is maintained during angioplasty. This art does not, however, seek to create a "bloodless" operative field during the performance of Carotid Endarterectomy, distinguishing the present invention from this art. This section of the catheter in the present invention may be composed of an elastic/elastomer/expandable material which, upon exposure to continuous blood flow under pressure, can expand to accommodate a greater flow of blood. This expandable component continues through the internal carotid balloon.

In another aspect of the invention, the catheter is provided with a series of apertures which are located along the shaft at a point prior/downstream from the common carotid balloon. These apertures encourage the blood flow, which has been interrupted by the inflation of the common carotid balloon, to be diverted into the lumen of the catheter, and to continue through the expandable portion and ultimately flow out of an aperture at the leading end of the catheter and into the lumen of the internal carotid artery beyond the internal balloon, thus creating a functional shunt which would provide continuous blood flow to the brain during the entire surgical procedure. The positioning and configurations of the apertures can be variable, and alternative embodiments can be conceived of and envisioned by those familiar with the art; all such embodiments would be incorporated within the spirit and scope of the invention.

In yet another aspect of the invention, a flow monitor is provided to the leading end of the lumen which uses fiberoptic, Doppler, nanotechnology, or any other technology known or acceptable to the art to measure the flow and/or pressure that blood flowing out of the leading end of the catheter and into the internal carotid artery perfusing the brain. It is anticipated that in the ideal embodiment, such a monitor would telemetrically communicate with an external receiver/printer which would provide the surgeon with a continuous record of blood flow to the internal carotid artery during the surgical intervention. Alternate embodiments of this sensor are conceivable, and can be envisioned by those familiar with the art; all such embodiments are incorporated within the spirit and scope of this invention.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
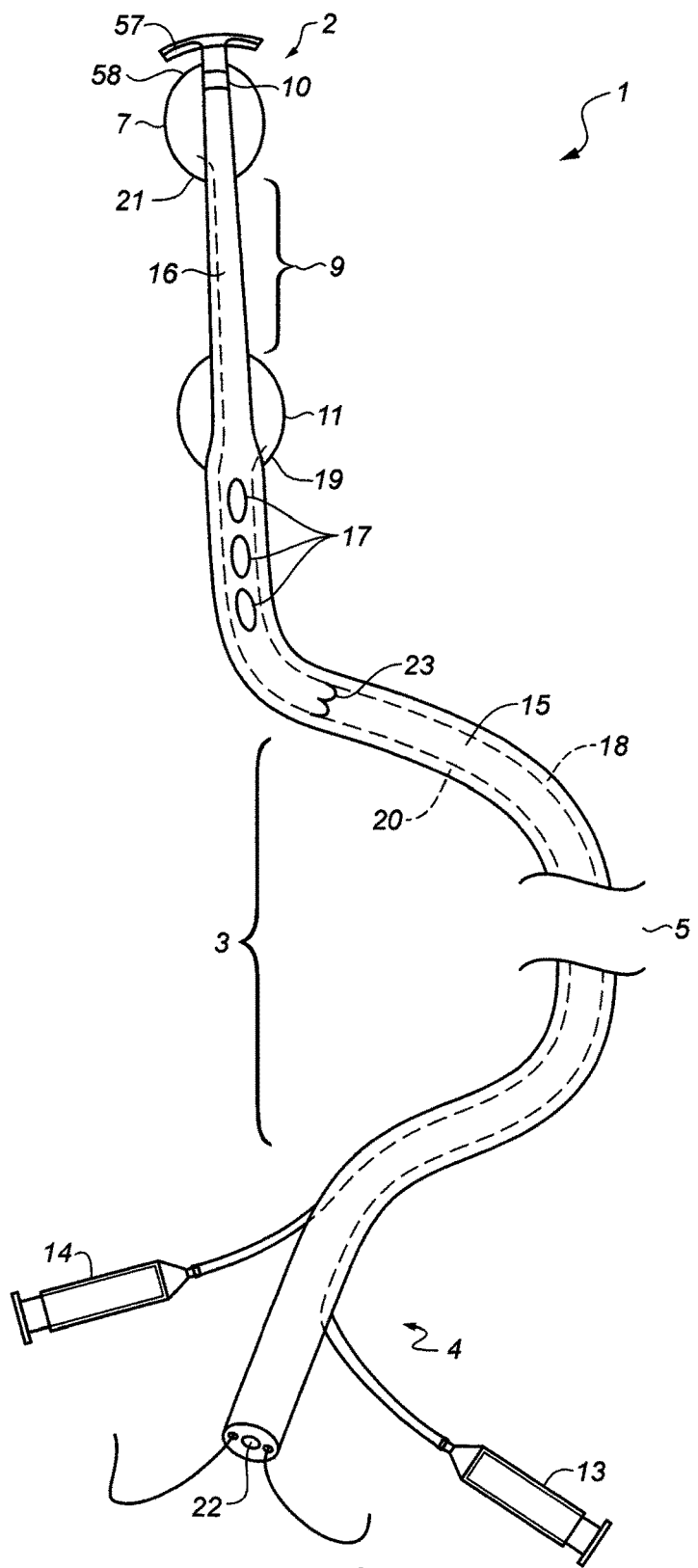
FIG. 1 is a diagrammatic representation of an embodiment of a catheter.

Referring now to FIG. 1 which is a general representation of a catheter 1, the catheter 1 is provided with a leading end 2, a central portion 3, and a trailing end 4. The catheter may be manufactured from a polymeric substance. The central portion 3 can be of varying lengths, and hence is shown with an interruption 5. The leading end 2 is provided with a number of unique features, beginning with a filtering net-like basket 58, which is actually the tip 57 of a guidewire used to place the catheter 1. A netting of the basket 58 is designed to capture embolic detritus which may break off or result from the surgical procedure. The leading end 2 of the catheter 1 is also provided with a nanosensor 10 which is designed to determine and document the blood flow being delivered. An internal carotid balloon 7 and a common carotid balloon 11 are fabricated from an elastomeric substance. The deployment of the netting 63 is described more completely in FIG. 6A to FIG. 6E below. An interval portion 9 of the catheter 1 that lies between the two balloons represents the actual functional shunt, and in one embodiment is comprised of expandable or elastomeric substance such that once the shunt is established, a substantial blood flow is maintained through the shunt. In concert with this, at the leading end 2 of the lumen of the shunt is the nanosensor 10 for measuring blood flow, as well as the pressure which is driving that blood flow. On the other side of the interval portion 9 is the common carotid balloon 11. The balloons 7 and 11 can be either spherical or somewhat elongated in configuration. In the embodiment of FIG. 1 the internal carotid balloon 7 is spherical while the common carotid balloon 11 is slightly elongated. At the trailing end 4 are found syringes 13, 14 which are used to control the inflation of the balloons 7 and/or 11. Syringe 13 is in continuity with lumen 18, which is a separate small lumen within the body of the catheter 1, and which through junction 19 is in continuity with the interior of the common carotid balloon 11, thus enabling the syringe 13 to inflate or deflate the common carotid balloon 11 by the injection of media into the balloon. Analogously, the syringe 14 is in continuity with lumen 20 which, in turn, is in continuity through junction 21 with the internal carotid balloon 7; thus, the syringe 14 can inflate and deflate this balloon by either injecting or withdrawing media from the balloon. The media can be air, fluids, silicon-based media or any other substance known to or acceptable to the art.

Aperture 22 is in continuity with a central lumen 15 through which contrast can be injected during insertion of the catheter 1. Furthermore, the catheter 1 may be inserted over a guidewire which passes through the central lumen 15. That portion of this central lumen 15 which is found in the internal portion 9 between the two balloons 7, 11 serves as the functional shunt 16 of the catheter 1. The catheter 1 is provided with multiple apertures 17, through which blood is carried with expansion of the common carotid balloon 11. In order to assure antegrade flow of the blood through the apertures 17 and into the shunt 16, a unidirectional valve 23 may be positioned in the central lumen 15 on the trailing side of the apertures 17.

Figure 2A:
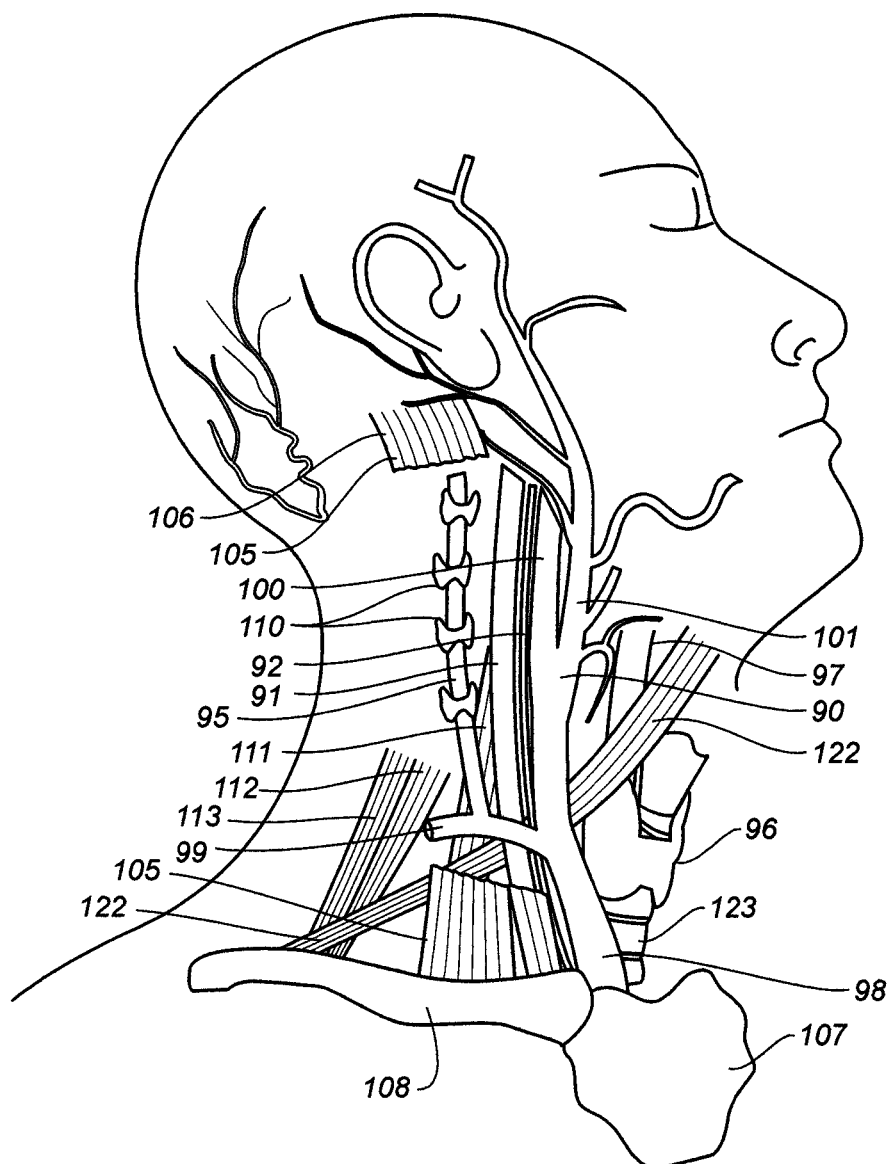
FIG. 2A depicts anterolateral aspects of a dissection of the structures of the neck demonstrating the right carotid artery system and associated structures.
Figure 2B:
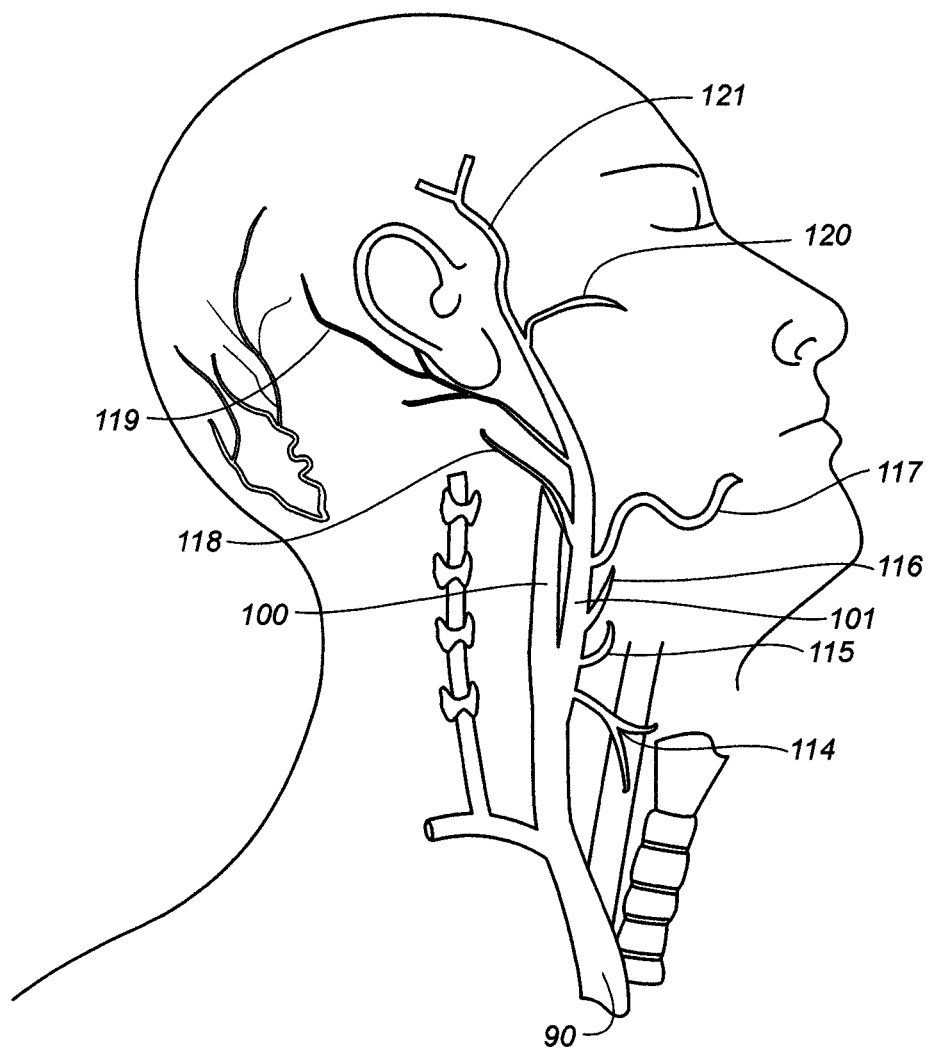
FIG. 2B depicts a right arterial tree including the eight common branches of the external carotid artery, as well as the course of the extracranial internal carotid prior to entering the base of the skull.

FIG. 2A depicts certain aspects of relevant normal and pathologic anatomy wherein the anterolateral aspect of the right side of the neck has been dissected by removal of the skin and superficial sheet of muscle known as the platysma. Furthermore, multiple muscles are demonstrated in a transparent motif, most particularly the prominent sternocleidomastoid muscle 105 which can be appreciated in most individuals as it extends from the mastoid process 106 cranially, bifurcating into two heads which attach to the manubrium of the sternum 107 medially and the clavicle 108 more laterally. The medial border of this muscle overlies the neurovascular bundle which includes the right internal jugular vein 91, the right vagus nerve 92, and the right common carotid artery 90; the relationships of these structures remain rather constant and are among of the most reliable anatomic landmarks. Also demonstrated in the transparent motif are the omohyoid muscle 122, as well as the anterior 111, medial 112 and posterior 113 scaleneus muscles, which lie superficial to the lateral aspect of the cervical vertebrae 110, through which the vertebral arteries 95 pass, with the left and right vertebral arteries ultimately joining together to form the basilar artery, which irrigates critical structures in the brainstem and continues to bifurcate into the posterior cerebral arteries and contributes to the circle of Willis (Not demonstrated). Medial to the carotid/jugular neurovascular bundle lie the important midline structures including the trachea 123, the thyroid gland 96 and the esophagus 97. The brachiocephalic artery 98 arises from the aortic arch (not shown), bifurcates into the right subclavian artery 99 and the common carotid artery 90. This artery ascends along the medial aspect of the sternocleidomastoid, and at approximately the C3-4, bifurcates into the internal carotid artery 100 and the external carotid artery 101. The former offers no branches within the neck and is directed through the base of skull (not shown) to pursue its intracranial course; the latter has a total of eight extracranial branches, which are demonstrated in FIG. 2B. This figure demonstrates the common carotid 90 arterial tree as it bifurcates into the internal carotid artery 100 and the external carotid artery 101. This figure further illustrates the eight typical branches of the external carotid artery 101, which include the Superior Thyroid 114, Ascending Pharyngeal 115, Lingual 116, Facial 117, Occipital 118, Posterior Auricular 119, Maxillary 120, and Superficial Temporal 121. It is this extensive arterial tree which provides the well-known richness of vascularity to the scalp.

Figure 3:
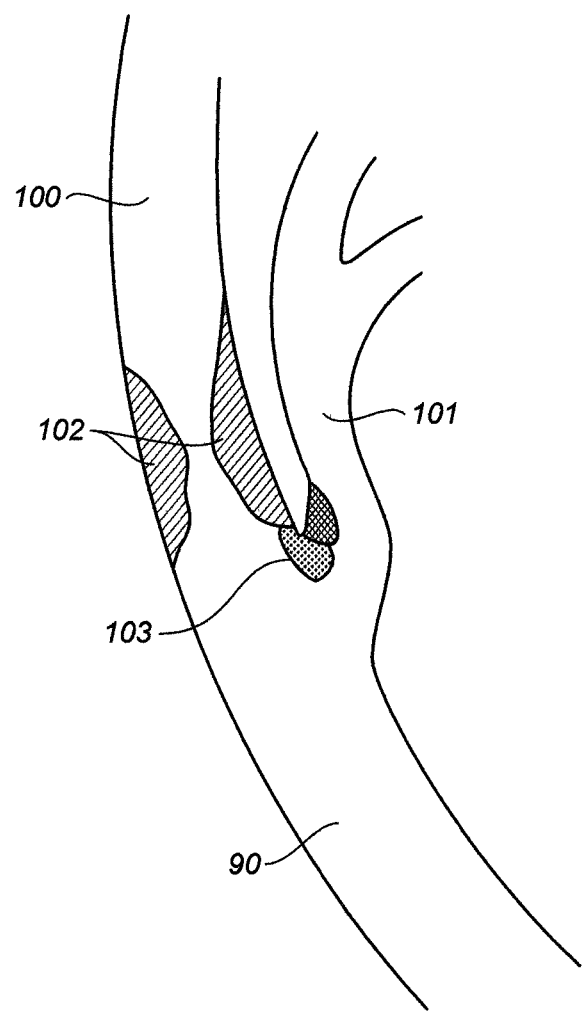
FIG. 3 is an anterior view of an isolated right carotid system, demonstrating typical plaque-stenosis.

In FIG. 3, a diagrammatic representation of an isolated right carotid system demonstrates the bifurcation of the common carotid artery 90 into the internal carotid artery 100 and the external carotid artery 101. The significant plaque-stenosis 102 is demonstrated at the takeoff of the internal carotid artery 100, with plaque disease occasionally extending to the bifurcation 103 itself (solid area) as well as the origin of the external carotid artery 101 (cross-hatched). The illustration herein demonstrates a narrowing of approximately 70%, which is widely considered to be the threshold for surgical intervention, particularly in symptomatic patients.

Figure 4A:
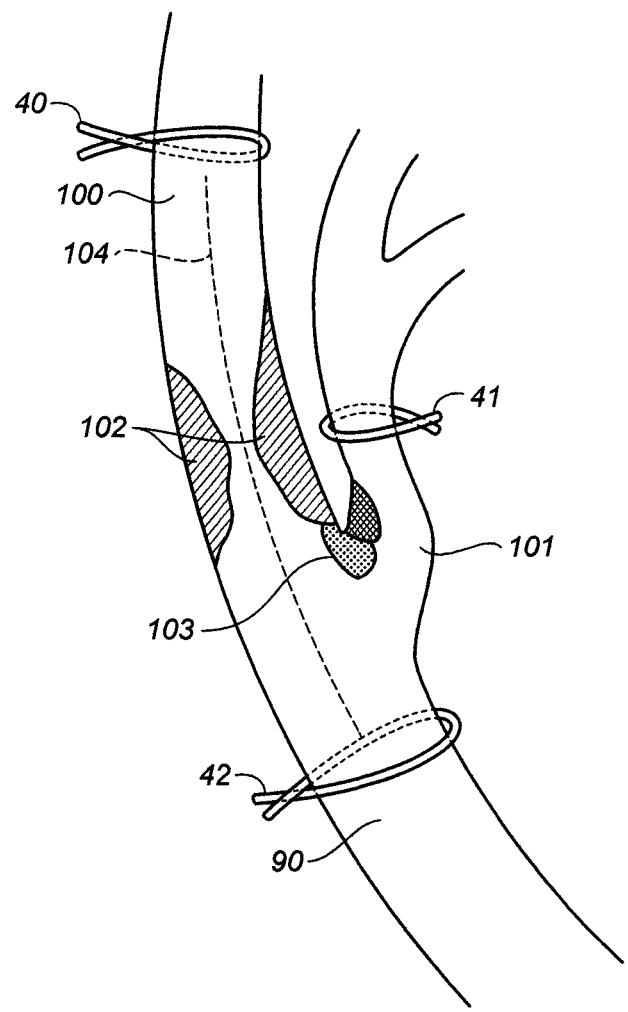
FIG. 4A is a diagrammatic representation of the right carotid system showing the site of the arteriotomy and, in FIG. 4B, the technique for removal of the plaque disease.
Figure 4B:
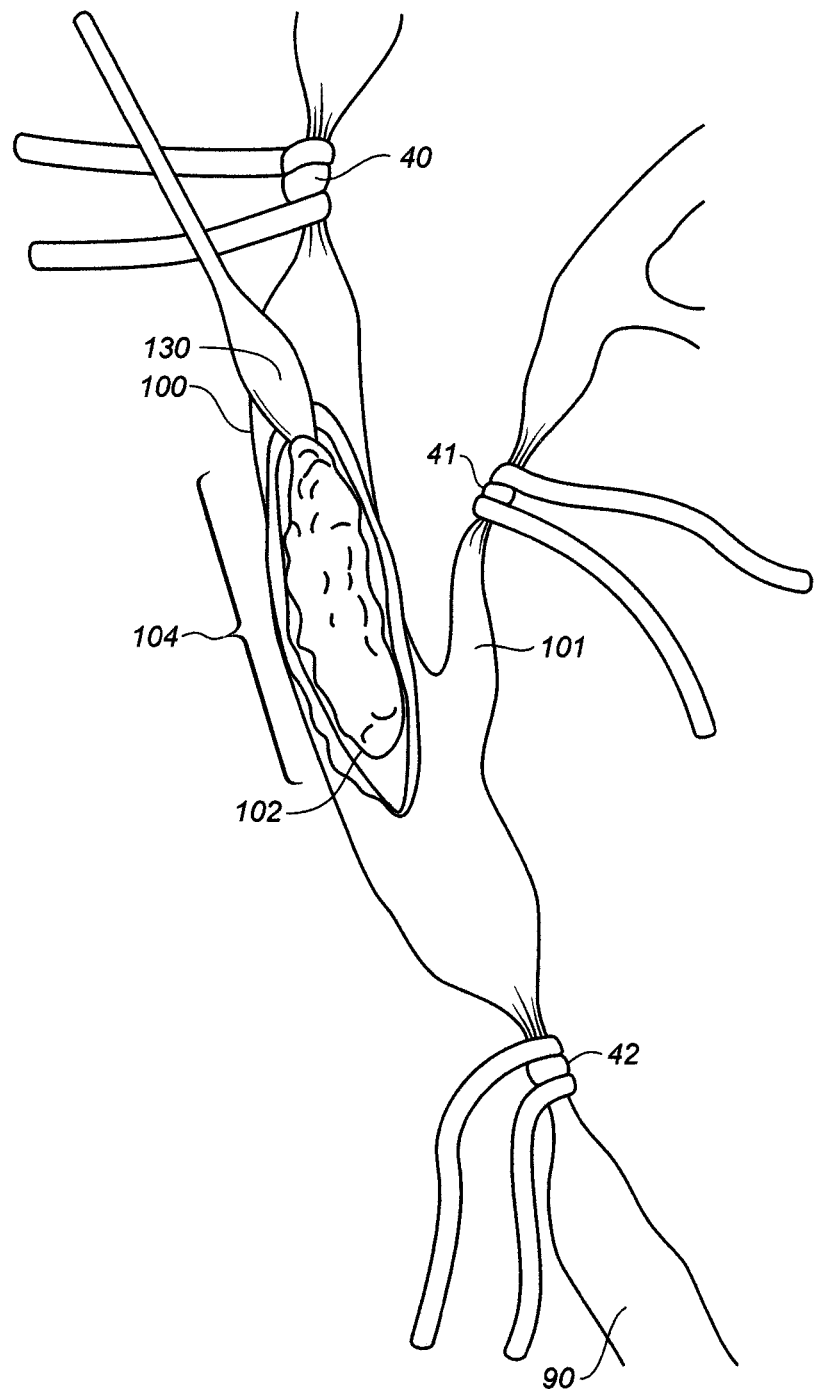

The current surgical technique used to treat such carotid disease is illustrated in FIG. 4A and FIG. 4B. In FIG. 4A, the site of the arteriotomy 104 is shown, as well as the sites where the common carotid artery 90, internal carotid artery 100, and external carotid artery 101 are occluded, typically by tying off with vascular tapes (42, 40 and 41 respectively), as shown here. In FIG. 4B, the arteriotomy 104 is opened, and the plaque-stenosis 102 is being removed with a dissector 130 using the technique of a classic endarterectomy. It can be seen that the internal carotid artery 100 is tied off with a vascular tape 40 as is the external carotid artery 101 with vascular tape 41 and the common 90, tied with vascular tape 42.

Figure 5A:
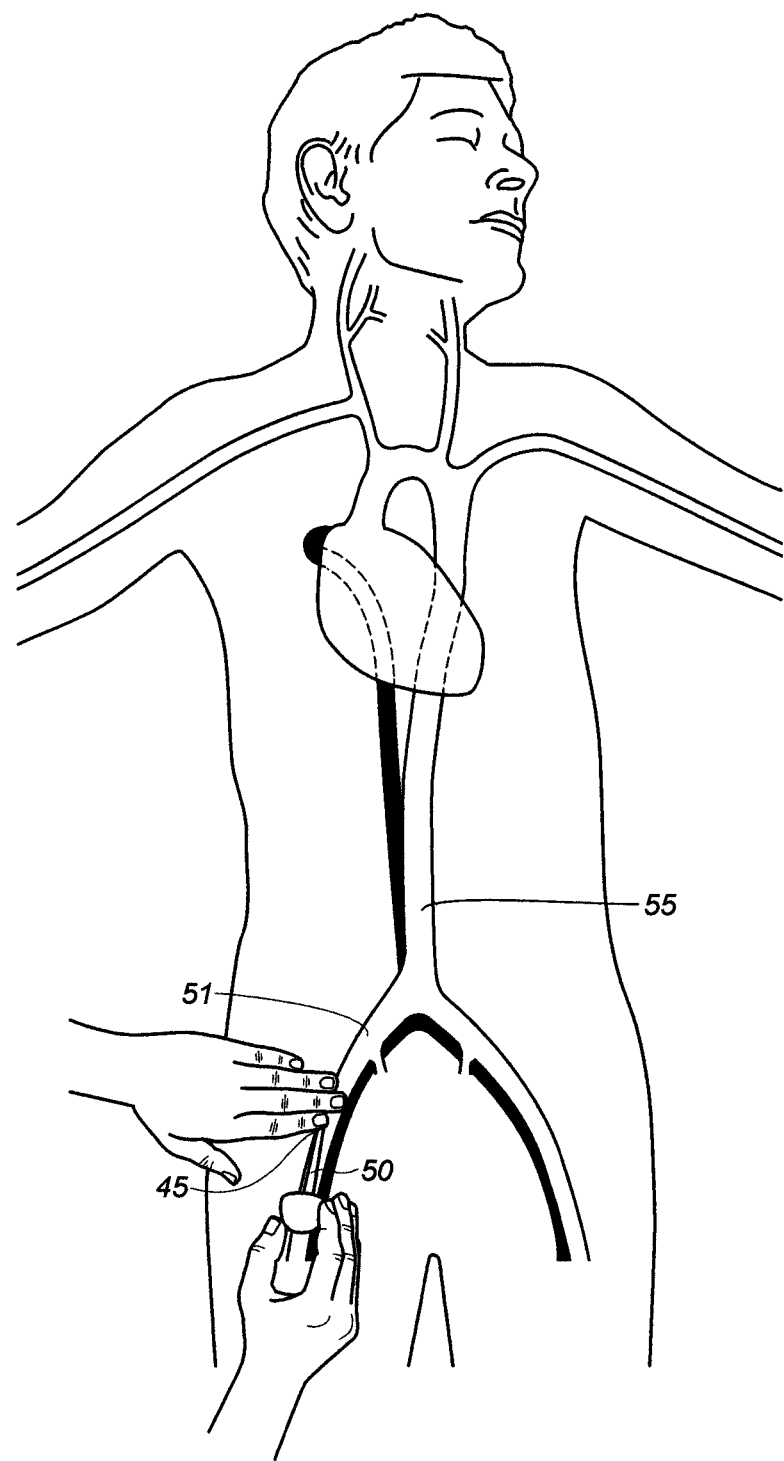
FIG. 5A is a diagrammatic representation of insertion of the catheter into the right carotid system using the Seldinger technique.
Figure 5B:
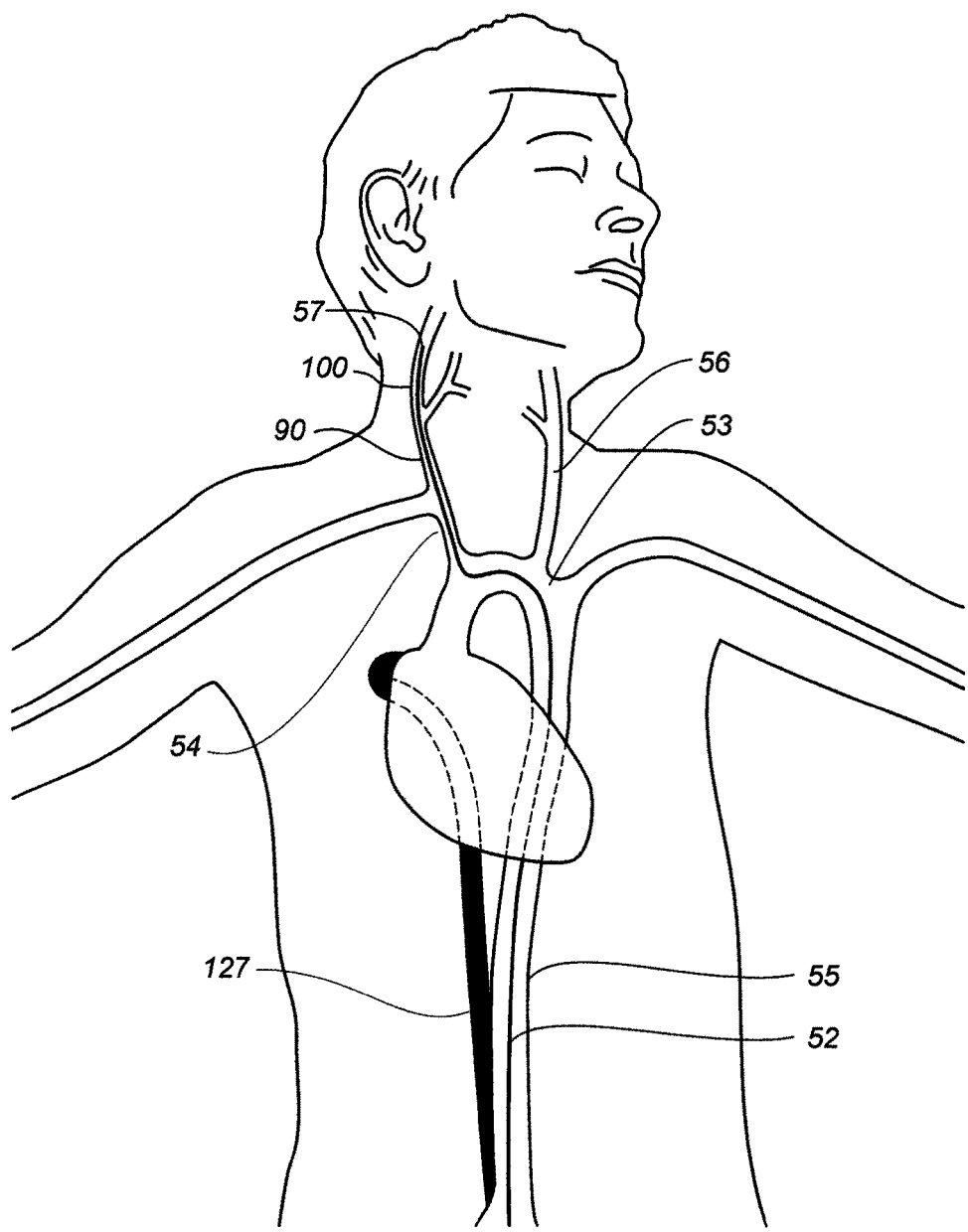
FIG. 5B is a diagrammatic representation of positioning of the catheter into the right carotid system using the Seldinger technique.

As shown in FIG. 5A, the catheter 1 herein disclosed may be inserted using a Seldinger technique. This has been established as a safe and effective way to place a diagnostic/therapeutic catheter into the arterial tree, including the carotid arteries. In FIG. 5A, this technique is diagrammatically illustrated, showing an example of an entry point 45 in the right groin (either groin can be used). A sheath 50 is placed after initial puncture of the (typically right) femoral artery 51. As shown in FIG. 5B, a guidewire 52 is then advanced in a retrograde fashion (against the blood flow) into the aorta 55. After the tip 57 of the guidewire 52 is passed through the arch 53 of the aorta, it is advanced in anterograde (same direction as the blood flow) into either the brachiocephalic artery 54 and then into the right common carotid artery 90 as in the illustrated instance, or the left common carotid 56, depending on the ultimate target. After being advanced into the right common carotid artery 90, it is ultimately advanced into the right internal carotid artery 100.

Figure 6A:
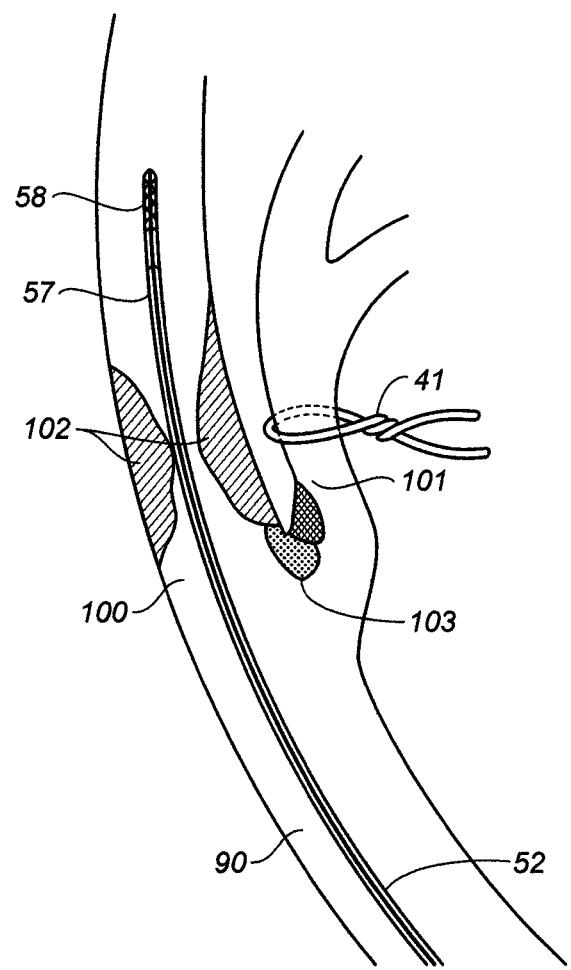
FIG. 6A to FIG. 6H depict passage of the leading end of the guidewire past the area of plaque-stenosis with the mechanism of deployment of the anti-embolic basket.

FIG. 6A shows the carotid artery system within the neck as the guidewire 52 is advanced into the desired position. As illustrated previously in FIG. 3, the origin of the internal carotid artery 100 just distal to the bifurcation of the common carotid artery 90 is the typical locus for the plaque-stenosis 102, again recalling that the plaque can extend to the level of the bifurcation 103, or even the origin of the external carotid artery 101, with plaque shown as the cross-hatched area. Isolating this section of the arterial system is necessary to achieve complete treatment of the disease. The external carotid 101 is again tied off with vascular tape 41 in the standard fashion, although an alternative embodiment utilizing a third lumen for positioning within this artery is conceivable. The leading end of the guidewire 52 is gently disposed through the area of the disease until the leading end 2, which has been provided with the deployable basket 58 to capture embolic detritus is positioned substantially beyond the area of the disease.

Figure 6B:
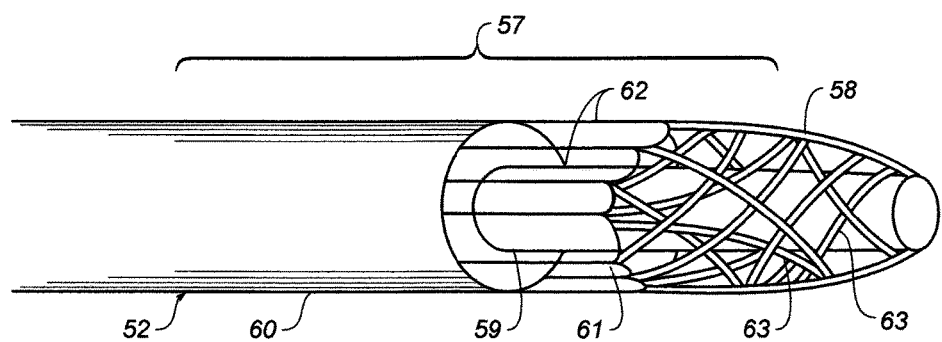

In FIG. 6B, FIG. 6C, FIG. 6D and FIG. 6E, the mechanism for deployment of the anti-embolic basket 58 is more completely illustrated. In FIG. 6B, an enlarged, lateral image of the isolated tip 57 of the guidewire 52 shows that the unique composition of the guidewire 52, in combination with the design of the deployable basket 58, allow for a unique, useful novel and nonobvious method to achieve deployment of the basket 58. The guidewire 52 is comprised of a central, internal wire 59 which is invested within an external tubular wire 60. In this view, the basket 58 is not yet deployed, being maintained in its primary position by a series of tethers 62 which extend from the leading end of the external tubular wire 60 to the periphery 61 of the deployable basket 58. The internal tubular wire 59 and external tubular wire 60 wires are configured such that they can be slidably repositioned with respect to one another. The deployable basket 58 is comprised of a netting 63 with fine apertures, which is attached centrally to the internal wire 59 (see, for example, FIG. 6C) of the guidewire 52. The netting 63 can be fabricated from either the same types of metal the wire is composed of (copper, nickel, aluminum) or it can be fabricated from polyester. It is important, however, that regardless of the material from which it is fabricated, that there is an element/scaffolding included which maintains a positional "memory," such that when the netting 63 is allowed to position itself by relaxation of the tethers 62, it returns to a position of function, which would be generally concave facing the flow of blood. Hence, emboli being carried along in the blood flow would be trapped by the netting 63.

Figure 6C:
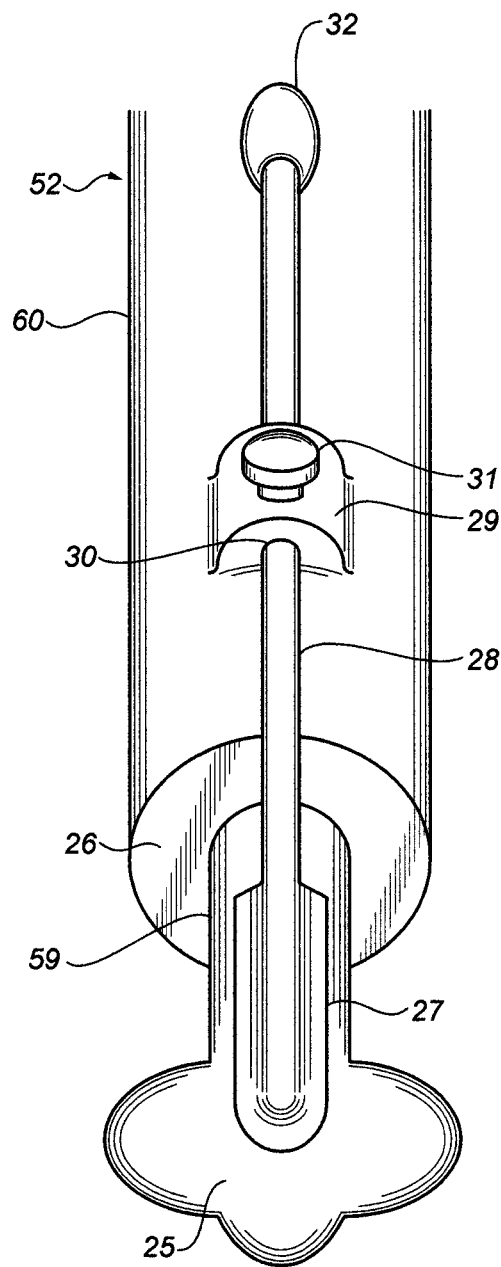

FIG. 6C is an enlarged, elevational view of the trailing end of the guidewire 52. The unique arrangement and relationship of the trailing end 25 of the internal wire 59 and the trailing end 26 of the external wire 60 ultimately provides for the deployment of the anti-embolic basket 58 (not shown in this picture). In this relationship, the trailing end 25 of the internal wire 59 protrudes beyond the trailing end 26 of the external wire 60. A platform 27 is provided. In one embodiment, the platform 27 is monolithic with the trailing end 25 of the internal wire 59 and has an extension 28 that is directed towards the external wire 60, being positioned adjacent and closely related to the external diameter of the external wire 60. A platform 29 is also seen arising from the external diameter of the external wire 60, the platform 29 being provided with an aperture 30. The platform 29 is positioned such that the extension 28 of the platform 27 of the internal wire 59 is disposed through the aperture 30. A fastening mechanism 31 is provided to the platform 29 arising from the external wire 60. The fastening mechanism 31 regulates the position of the extension 28, which continues beyond the aperture 30 of the platform 29 arising from the external wire 60. A leading end 32 of the extension 28 is enlarged, acting as a stop during deployment of the basket 58. These actions will be elucidated below.

Figure 6D:
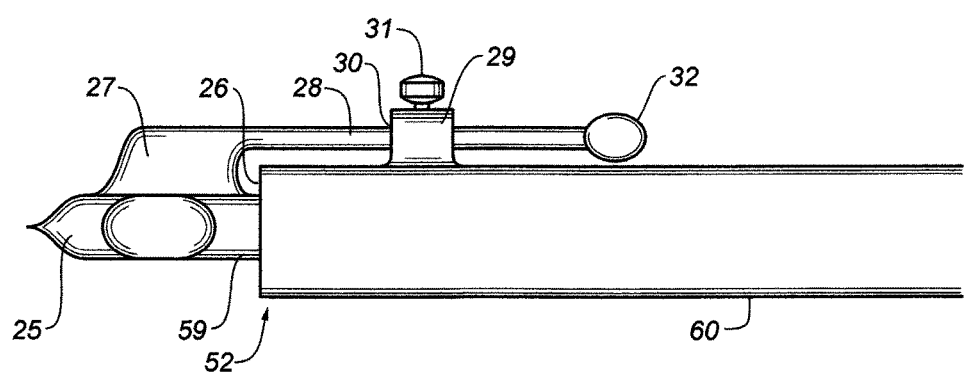

FIG. 6D further depicts the structures of the trailing end of the guidewire 52 in this lateral view. Again it can be seen that the trailing end 25 of the internal wire 59 extends beyond the trailing end 26 of the external wire 60. The platform 27 arising from the internal wire 59 is readily appreciated in this perspective, as is the extension 28 which is directed towards the central portion of the guidewire 52, with the extension 28 being disposed through the aperture 30 (projected on end) of the platform 29 arising from an external surface of the external wire 60. The position of the extension 28 is controlled by a fastening mechanism 31 inserted into the platform 29 arising from the external wire 60. The enlargement of the leading end 32 of extension 28 can also be seen in this depiction. Furthermore, it can be seen that if the external wire 60 is advanced towards the leading end of the internal wire 59, the platform 29 will be advanced along extension 28 until it reaches the enlargement which acts as a stop. The distance between the leading side of the platform 29 and the beginning of the enlargement correlates with the distance required to advance the leading end of the external wire 60 sufficiently to completely relax the tethers 62 (not shown in this image), thus allowing the basket 58 (also not shown) to deploy.

Figure 6E:
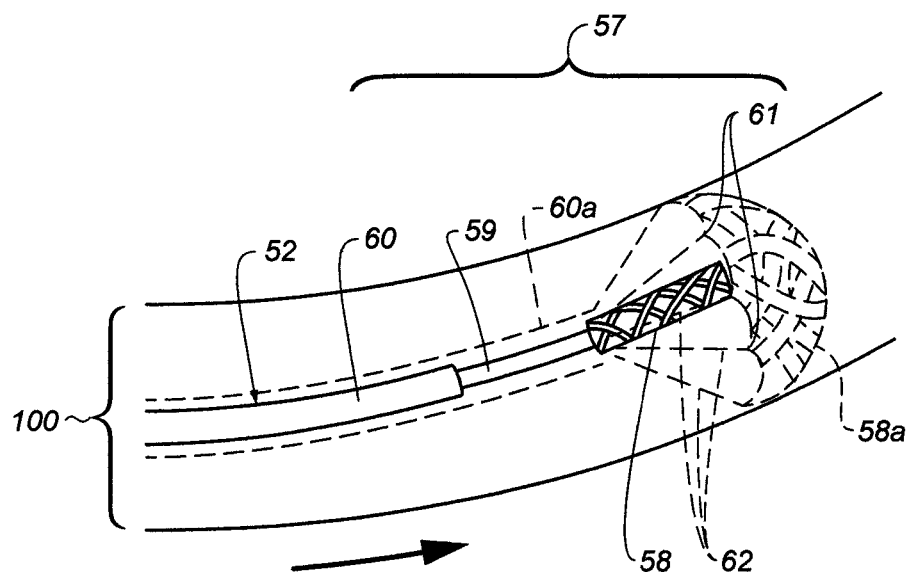
Figure 6F:
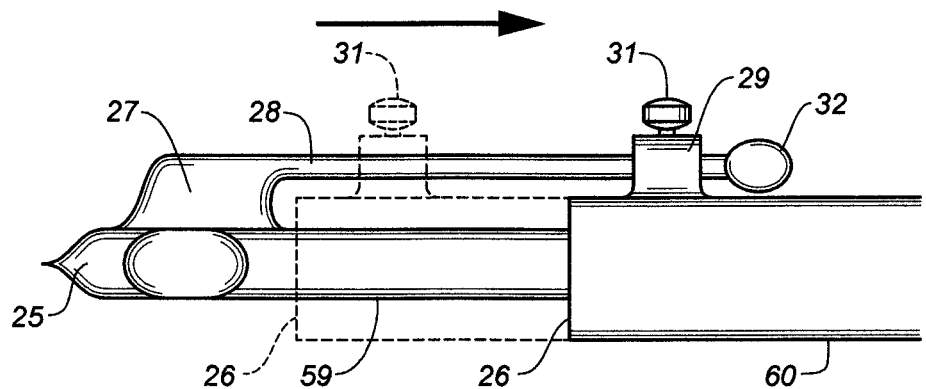

FIG. 6E and FIG. 6F demonstrate the interplay of the trailing ends 25, 26 of the internal and external wires 59, 60, result in deployment of the basket 58, resulting in the anti-embolic action. FIG. 6E demonstrates the tip 57 of the guidewire 52 within the internal carotid artery 100. The leading end of the external wire 60 can be seen advancing towards the leading end of the internal wire 59; the advancing external wire 60 is depicted by the lines 60a, and moves in the direction indicated by the arrow. For illustrative purposes, the ghosted image of the external wire 60 which is translated is depicted as slightly larger than the depiction of the non-deployed external wire 60. The non-deployed basket 58 is seen at the leading end of the internal wire 59. In FIG. 6F the simultaneous actions at the trailing ends 25, 26 of the internal wire 59 and the external wire 60 contribute to the actions occurring at the tip 57 of the guidewire 52. Specifically, in this lateral view, the trailing end 26 of the external wire 60 can be translated with release of the fastening mechanism 31 in platform 29, which secures the extension 28. With release of the fastening mechanism 31, the external wire 60 can be translated along the internal wire 59 towards the leading end as shown in FIG. 6E. In FIG. 6F this transposition is again in the direction indicated by the arrow, with the transposition of the external wire limited by the interface of the platform 29 with the enlarged leading end 32 of extension 28. The transposition can be further understood as shown by the dotted lines depicting the trailing end 26 of the external wire 60 and the platform 29. Dotted lines from numbers to aspects of the image further indicate the original positions of the structures prior to the translation. At the leading end, as shown in FIG. 6E, external wire 60 is advanced toward the leading end of the internal wire 59, as indicated by the arrow. As the transposed external wire 60a approaches leading end of the internal wire 59, the tethers 62 are relaxed. This allows the memory component of the netting 63 to return to its primary configuration, and in that way the basket 58a can be deployed and expand into its fully deployed configuration. It is anticipated that the basket could be, and in the preferred embodiment would be coated with an anticoagulant to further help reduce/ break up and emboli comprised of blood clot.

Figure 6G:
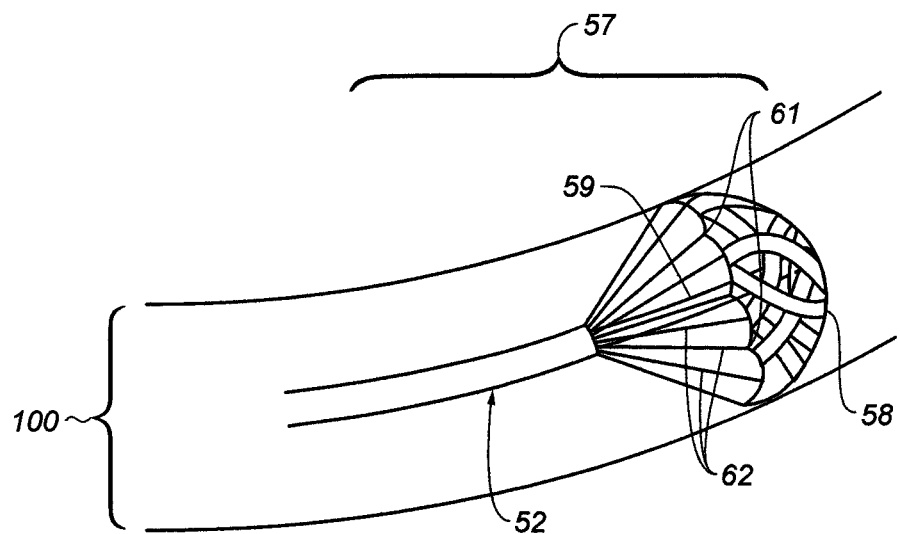
Figure 6H:
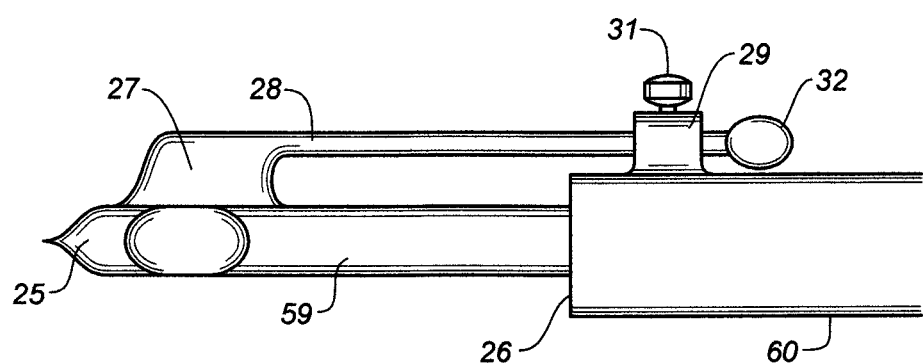

FIG. 6G shows the final position of the fully deployed basket 58 at the tip 57 of the guidewire 52 within the internal carotid artery 100. The external wire 60 has been advanced towards the leading end of the internal wire 59 until the tethers 62 are radially dispersed allowing the basket 58 to be fully expanded, with the netting 63 being completely brought against the internal surface of the artery. The internal wire 59 continues to the central portion of the basket 58. FIG. 6H shows the final position of the trailing end 25 of the internal wire 59 with respect to the final position of the trailing end 26 of the external wire 60. Platform 27 gives rise to the extension 28 which is disposed through aperture 30 (not seen) in platform 29. This configuration has allowed the external wire 60 to advance toward the leading end of the internal wire 59, with the enlargement 32 serving to arrest the advance of the external wire. It is noted that in this position, the fastening mechanism 31 is in a "locked," position so that the basket 58 on the leading end is not prematurely or inadvertently reconfigured or returned to its primary position.

Figure 7:
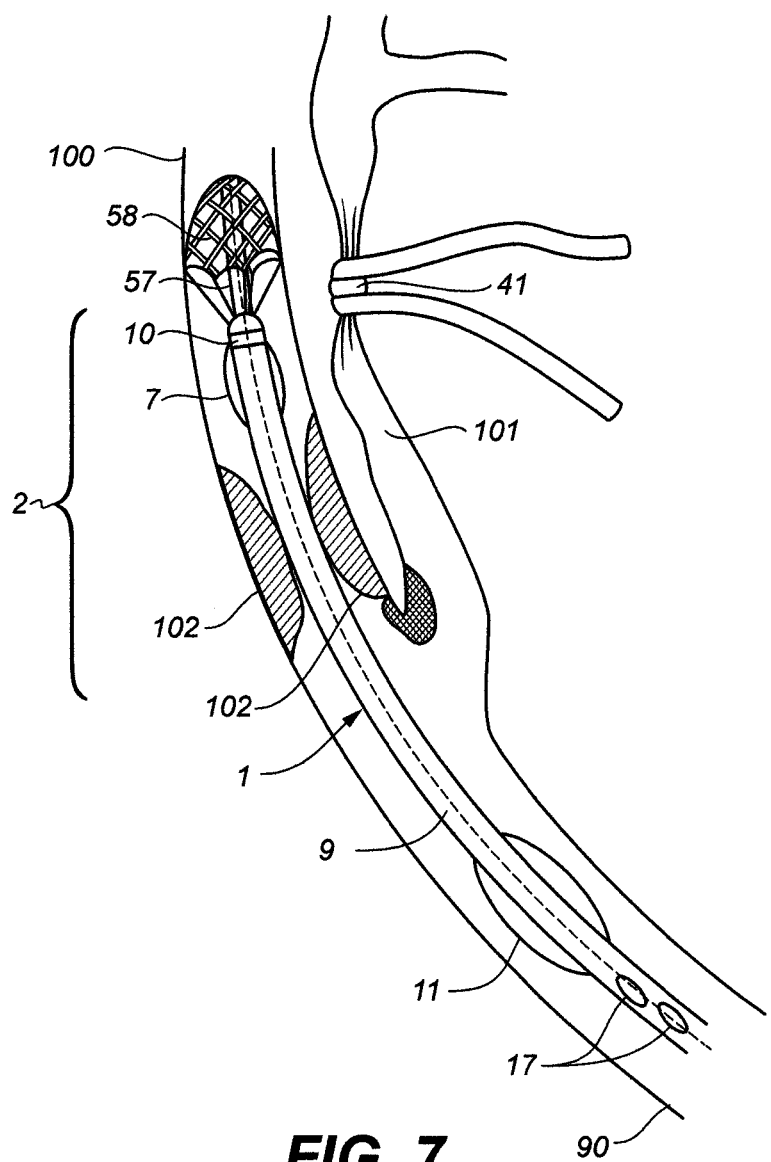
FIG. 7 illustrates passage of catheter over guidewire prior to deployment of the internal carotid and common carotid balloons.

With reference to FIG. 7, after final positioning of the tip 57 with expansion of the basket 58, the catheter 1 is disposed over the guidewire 52. The tip 57 is seen extending beyond the leading end 2 of the catheter 1. FIG. 7 demonstrates the leading end 2 of the catheter 1 having been positioned. The common carotid balloon 11 and internal carotid balloon 7 have not yet been expanded within their target arteries, and are seen on the sides of the catheter 1. The central shunt portion of the catheter 1 is seen extending beyond the plaque-stenosis 102. With the occlusion of the arteries by the balloons 7, 11 a "bloodless" field is created which allows the surgical intervention to proceed, as outlined below. As will be demonstrated below, with the inflation of the common carotid balloon 11, the apertures 17 will become active, shunting blood from the common carotid artery 90 through internal portion 9 and conducting blood to the internal carotid artery 100. As previously discussed, the unidirectional valve (not demonstrated in this image) prevents blood from backflowing into the catheter 1. A nanosensor 10 is provided to the leading end 2 of the catheter 1. Using microtechnology and/or nanotechnology, this sensor provides a measurement of blood flow as well as the pressure under which the blood is flowing. The external carotid artery 101 is tied off with vascular tape 41 prior to the origin of the first branch, the superior thyroid artery 114.

Figure 8:
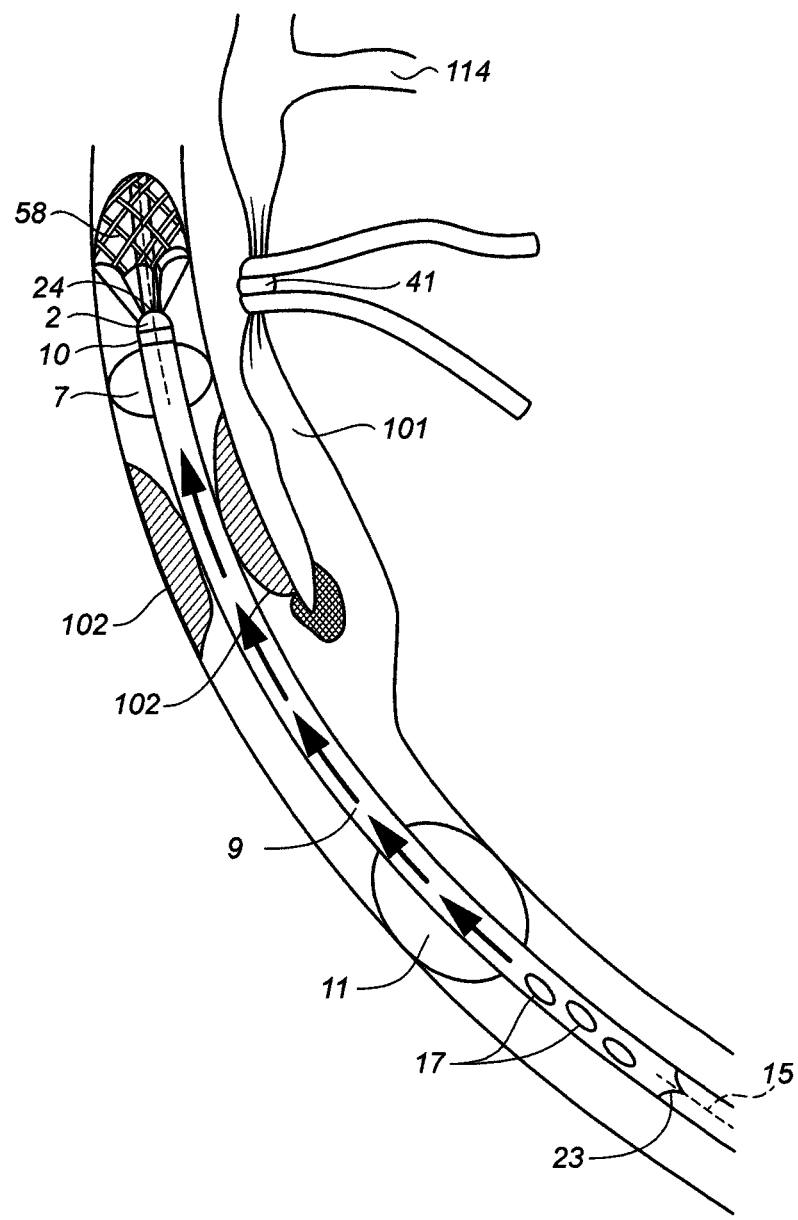
FIG. 8 depicts deployment of the common carotid balloon with opening of the shunt.

In FIG. 8, the expansion of the common carotid balloon 11 results in the blood being preferentially diverted into the apertures 17 and subsequently through the internal portion 9 (as indicated by the arrows) past the area of the plaque-stenosis 102, ultimately maintaining continuous cerebral flow upon exiting through the aperture 24 at the leading end 2 of the catheter 1. In the embodiment of FIG. 8, a single aperture 24 is shown. In other embodiments, more than one aperture is present. This flow is measured by the nanosensor 10 and transmitted to an outside recorder (not shown) documenting continuous blood flow during the entire procedure. The basket 58 remains intact to capture any embolic debris that could occur as the result of the catheter's presence. To assure anterograde flow and prevent backflow of blood through the trailing end of the catheter (not shown), a unidirectional valve 23 has been provided to the central lumen 15 of the catheter 1. The internal carotid balloon 7 has also been deployed. The external carotid artery 101 remains occluded by vascular tape 41, prior to the takeoff of the first branch, the superior thyroidal artery 114.

Figure 9:
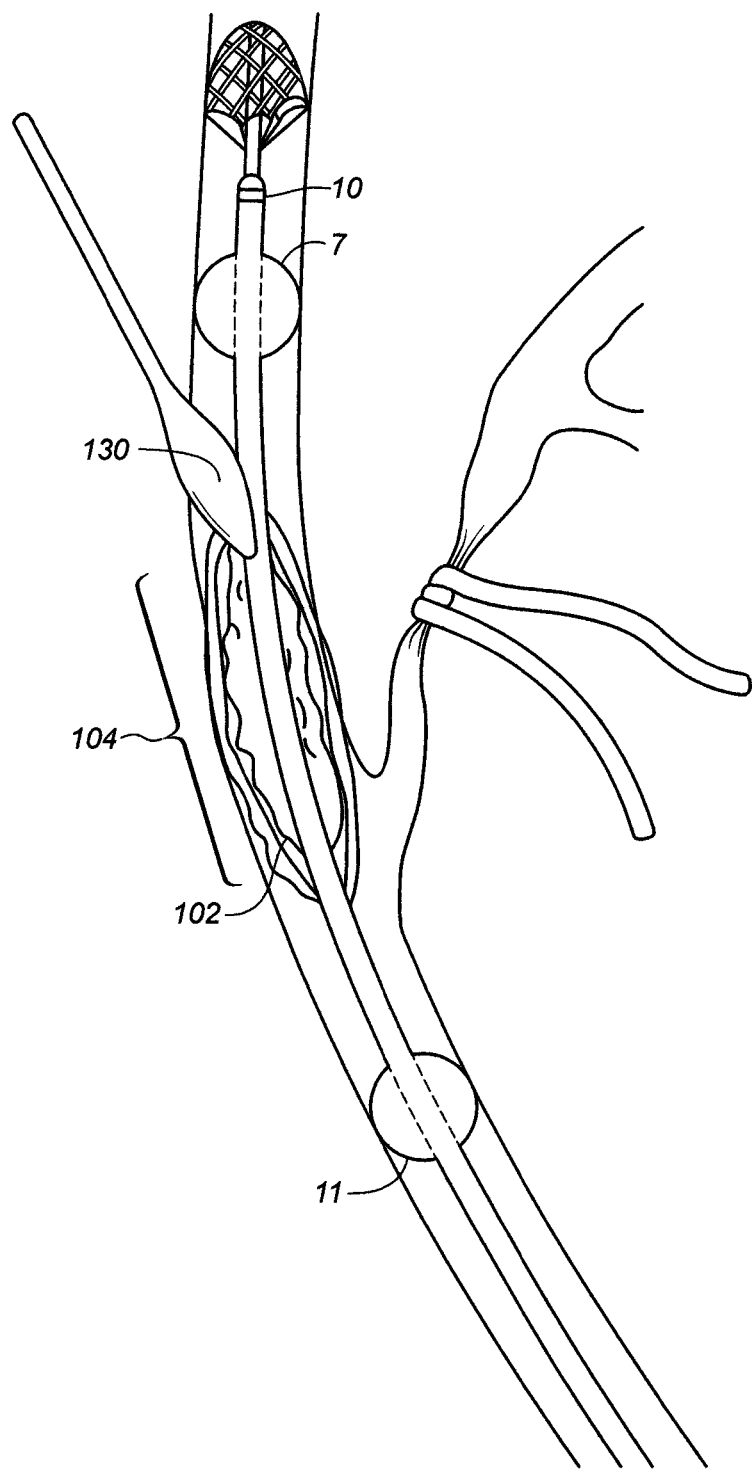
FIG. 9 illustrates removal of plaque-stenosis with sa hunt in place and retention of filtering mesh.

FIG. 9 shows the actual endarterectomy being performed through an arteriotomy (incision of the artery) 104, with the dissector 130 removing the plaque-stenosis 102 from the artery. The shunt portion of the catheter is seen in the center of the operative field; however, surgeons can easily work around this device. Blood flow has never been interrupted, and has been documented by the sensor 10. The internal carotid balloon 7 and common carotid balloon 11 are inflated and maintain a bloodless field, along with the vascular tape 41.

Figure 10:
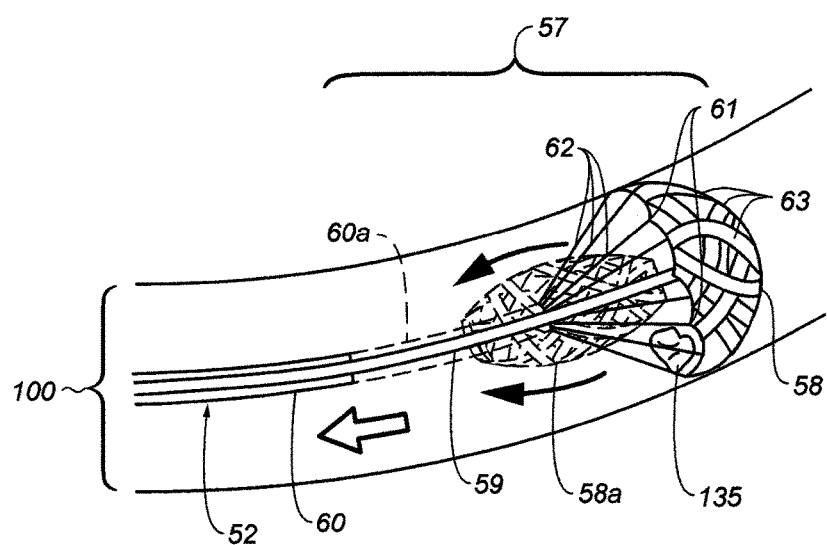
FIG. 10 depicts collapse of the filtering mesh and removal of the catheter.

FIG. 10 is an image of the tip 57 of the guidewire 52 within the internal carotid artery 100, illustrating that upon completion of the procedure, the basket 58 is collapsed by repositioning the external wire 60 towards the trailing end of the internal wire 59, as indicated by the direction of the open arrowhead. This is further illustrated by the dotted lines, representing the deployed position of the external wire 60a. The solid lines 60 show the final position of the external wire. This repositioning draws the tethers 62 centrally, which uniformly pulls on the circumference of the netting 63 causing it to collapse around the leading end of the internal wire 59. This repositioning, in turn, serves as an actuator causing the basket 58 to collapse encircling the leading end of the internal wire 59, as demonstrated by the curved solid arrows. The final position of the basket 58 prior to removal is indicated by the ghosted image in dotted lines 58a. Any emboli 135 which may have been trapped within the basket 58 are now secured into final position for retrieval upon removal of the guidewire 52 and catheter 1 from the insertion site in the groin at the end of the case (not shown).

Figure 11:
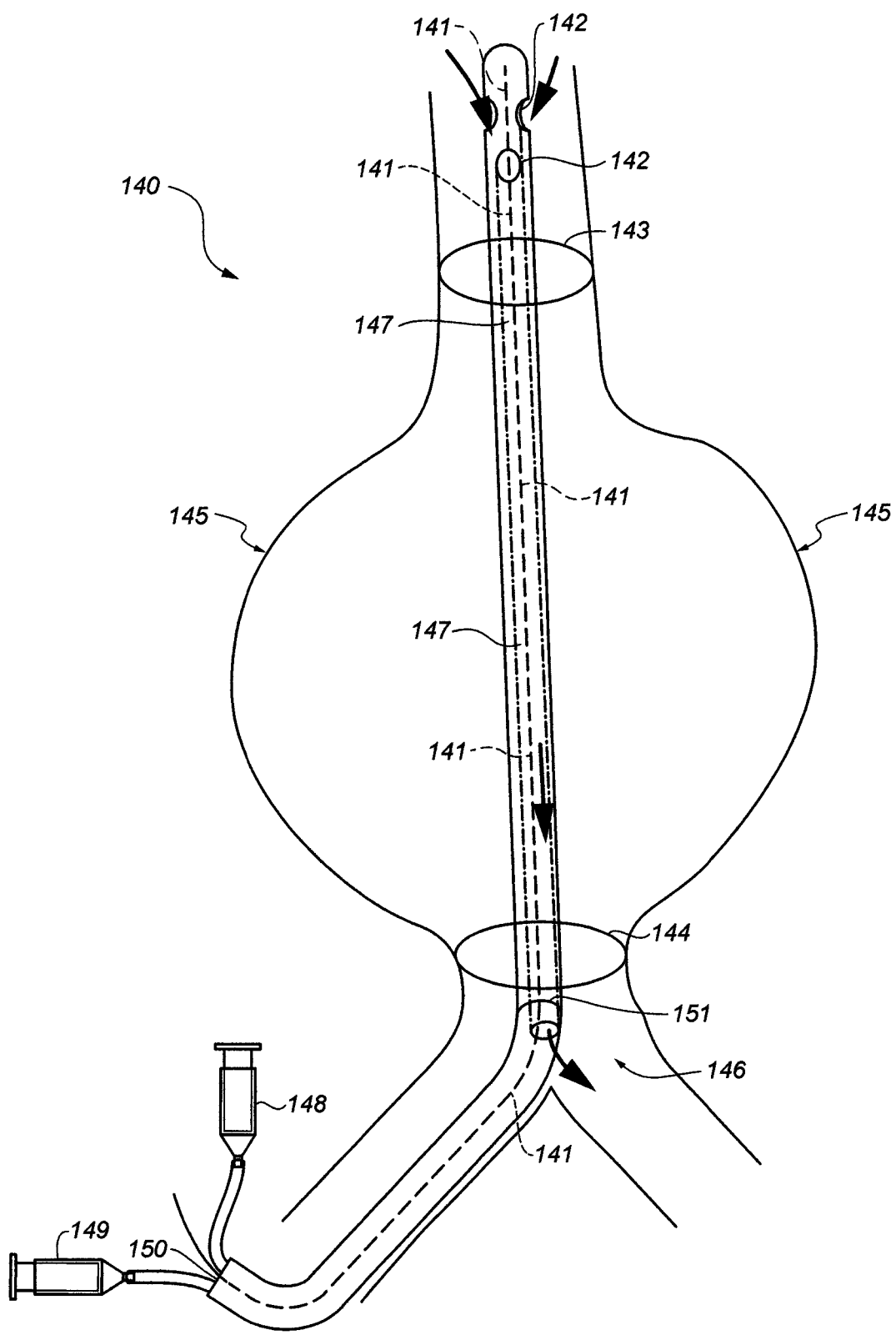
FIG. 11 is an illustration of an alternative embodiment of a catheter showing reversal of the shunt useful in treatment of lesions such as abdominal aortic aneurysm.

FIG. 11 shows an alternative embodiment of a catheter 140 which is inserted over a guidewire 141. The positioning of the catheter 140 is such that the flow through the shunt is not directed towards the leading end, as in the embodiment described above. Instead, in this embodiment, apertures 142 are positioned beyond the occluding balloon which is found on the leading portion 143 of the catheter 140. The blood enters the apertures 142 (as indicated by the arrows) and flows through the central channel 147 exiting from the trailing portion 146 of the catheter 140, beyond the trailing balloon 144. As the blood flows out of the trailing portion 146 of the central portion of the catheter 140, a flow sensor 151 measures the blood flow and/or pressure under which the flow proceeds. The balloons would again be inflated with the use of syringes 148, 149 at the trailing end 150 of the catheter. The syringes 148, 149 are connected to minor lumina within the walls of the catheter (not shown in this image), which are ultimately connected to the balloons, and which transfer media to the balloons in order to inflate them. As previously stated, the media could be air, water, silicon-based media, or any other substance known or acceptable to the art. This embodiment could be useful in pathologies such as ruptured abdominal aortic aneurysms 145, thus preserving blood flow through the catheter to points beyond the distal aorta.

Figure 12:
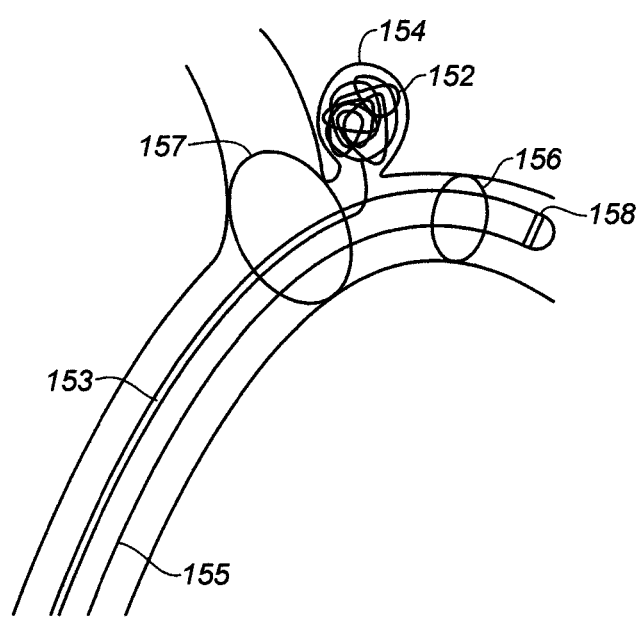
FIG. 12 depicts a catheter useful during coiling treatment of intracranial aneurysms.

FIG. 12 is an iteration which reflects the potential for use in the endovascular treatment of intracranial aneurysms. The treatment of such aneurysms frequently involves placement of a wire coil 152 into the aneurysm 154. In this image of this iteration, the catheter 155 is within a cerebral artery, wherein a separate lumen 153 allows for the delivery of such a coil into the aneurysm 154. The balloons in this catheter 155 are designed to have a malleable configuration so that balloons 156 and 157 are able to conform to the local anatomy, in particular the relationship with local vessels such as in this example, whereby the trailing balloon 157 occludes another local vessel which is feeding the distal cerebral structures. The system herein disclosed allows for coiling the aneurysm while excluding the aneurysm from circulation and maintaining continuous flow, as measured by the flow sensor 158. A major complication of this type of aneurysm treatment is rupture of the aneurysm with consequent severe bleeding. Use of the catheter controls such bleeding until definitive surgical intervention could be achieved.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An endovascular catheter comprising:
    a flexible lumen with a leading end, a trailing end and a central portion disposed between the leading end and the trailing end;
    a first syringe and a second syringe, each disposed proximate the trailing end;
    at least one aperture in the central portion, the at least one aperture being fluidly connected to an opening at the leading end thereby providing a bypass;
    a common carotid balloon operatively connected to the first syringe;
    an internal carotid balloon operatively connected to the second syringe;
    a concave extendable netting at the leading end;
    a guidewire extending through the flexible lumen from the trailing end to the leading end; and
    a platform;
    wherein the guidewire is operatively connected to the extendable netting to extend the extendable netting outside of the flexible lumen to form a net and the internal carotid balloon is disposed proximate the leading end and the common carotid balloon is disposed between the internal carotid balloon and the at least one aperture, the internal carotid balloon and the common carotid balloon being spaced apart by a distance;
    wherein the guidewire has a terminus proximate the trailing end of the flexible lumen, the guidewire having an external tubular wire and an internal wire that is slidably disposed within the external tubular wire, wherein the internal wire is operatively connected to the extendable netting to extend the extendable netting outside of the flexible lumen to form the net;
    wherein the internal wire comprises an extension at the terminus that extends outside of, and along an outside of, the external tubular wire; and
    wherein the extension passes through a hole in the platform, the extension having an enlarged tip that is larger than the hole that limits motion of the extension.

2. The endovascular catheter as recited in claim 1, further comprising a blood flow sensor disposed at the leading end that monitors blood flow through the at least one aperture.

* * * * *